United States Patent
Gallas

(10) Patent No.: US 12,350,197 B2
(45) Date of Patent: Jul. 8, 2025

(54) LIGHT FILTER FOR REPAIRING THE RETINA

(71) Applicant: Photoprotective Technologies Incorporated, San Antonio, TX (US)

(72) Inventor: James M. Gallas, San Antonio, TX (US)

(73) Assignee: Photoprotective Technologies Incorporated, San Antonio, TX (US)

( * ) Notice: Subject to any disclaimer, the term of this patent is extended or adjusted under 35 U.S.C. 154(b) by 161 days.

(21) Appl. No.: 18/136,339

(22) Filed: Apr. 19, 2023

(65) Prior Publication Data

US 2023/0255828 A1    Aug. 17, 2023

Related U.S. Application Data

(62) Division of application No. 16/847,649, filed on Apr. 13, 2020, now Pat. No. 11,672,703.

(60) Provisional application No. 62/832,385, filed on Apr. 11, 2019.

(51) Int. Cl.
*A61F 9/007* (2006.01)
*A61F 9/00* (2006.01)
*A61N 5/06* (2006.01)
*G02C 7/10* (2006.01)
*C09K 11/00* (2006.01)

(52) U.S. Cl.
CPC .......... *A61F 9/0079* (2013.01); *A61F 9/0017* (2013.01); *A61N 5/06* (2013.01); *G02C 7/104* (2013.01); *A61N 2005/0661* (2013.01); *C09K 11/00* (2013.01); *G02C 7/107* (2013.01)

(58) Field of Classification Search
CPC ....... A61F 9/0079; A61F 9/0017; A61N 5/06; A61N 2005/0661; A61N 2005/0659; A61N 2005/0662; G02C 7/104; G02C 7/107; G02C 2202/10; C09K 11/00
See application file for complete search history.

(56) References Cited

U.S. PATENT DOCUMENTS 9,517,126 B2 * 12/2016 Wiechmann ............... A61F 2/14
9,726,910 B2 *  8/2017 Gallas ..................... G02B 5/223

* cited by examiner

*Primary Examiner* — Tuyen Tra

(57) ABSTRACT

The detailed characteristics of the red fluorescence of the human lens—that occurs at the seventh decade of life—is recognized as an example of evolutionary photobiomodulation for repair of the retina, and then used as a paradigm for extending current parametric values for reproducible photobiomodulation. The new photobiomodulation parameters involve relative intensities for wavelength bands within the range of 600 nm to 900 nm.

1 Claim, 6 Drawing Sheets

LIGHT FILTER FOR REPAIRING THE RETINA

RELATED PRIORITY DATE APPLICATION

This application is a divisional application of co-pending U.S. patent application Ser. No. 16/847,649 filed on Apr. 13, 2020 which claims the benefit under 35 U.S.C. 119(e) of the U.S. provisional application No. 62/832,385 filed on Apr. 11, 2019.

FIELD OF THE INVENTION

The present invention relates to the field of light filters that provide repair to the eyes and skin through the process of photobiomodulation. Still more particularly, the present invention relates to ophthalmic lenses and light filters whose emission spectrum is that of the red fluorophore of the aged human lens.

BACKGROUND OF THE INVENTION

Photobiomodulation, also called PBM, is a therapeutic technique that involves exposure of humans to red and near infrared wavelengths of light to heal, repair and improve health. Interest in PBM is growing rapidly because its implementation is noninvasive and safe. However, positive outcomes of PBM have been hampered by the persistent challenges of reproducibility of the positive health benefits repeatedly reported for PBM.

Those skilled in this art underscore the importance of specific physical parameters, and their range of values, for the light source in order to achieve reproducibility and positive PBM health benefits. Up to now, these parameters have primarily been:
1) the wavelengths and wavelength regions
2) the intensity delivered to the subjects
3) The dose delivered to the subject
4) Fluences Most of the research investigations relating to PBM to treat the retina for repair of macular cells have used 670 nm light from LED light sources. Other wavelengths between 600 nm and 1000 nm were used but most studies used 670 nm light.

The possible combination of the parameters listed in 1) to 4) is very large making optimization of a positive PBM effect a challenge.

An essential feature of the resent invention is that there is very little agreement among those skilled in the art regarding the values of the aforementioned parameters, or their range of values, in a manner that completely or fully supports a positive PBM outcome. Yet there are many positive outcomes from PBM treatment.

U.S. Pat. No. 9,726,910 to James M. Gallas discloses an ophthalmic lens that enhances the filtered sunlight in the UV and visible and UV region of wavelengths and then converts the energy absorbed into fluorescence with emission bands of wavelength width that mirror the absorption bands of cytochrome C.

The present invention discloses a filter that effects photobiomodulation and repair of the retina.

These and other advantages of the present invention will become apparent from the following description and drawings.

SUMMARY OF THE INVENTION

An objective of this invention is the description of an ophthalmic lens or a light filter that provides a broad improvement to the successful outcome of PBM for the repair of the retina. It is an essential objective of this invention that the use of an additional and new physical parameter for light sources for PBM are modeled after the fluorescence emission spectrum of the human lens in its seventh decade of life. This spectrum is displayed in FIG. 2. In arriving at this improvement this invention directs attention and consideration to the following:
1. A search for endogenous chromophores as potential fluorophores for PBM;
2. That if such endogenous fluorophores could be identified, their photophysical and photochemical characteristics would presumably be in accord with both evolutionary development as well as the agenda for PBM, that is, repair;
3. That such fluorophores should occur wherever there is damage; this is reasonable because repair would require some proximity to damage;

Such an endogenous fluorophore was reported by NT Yu (Invest Ophthalmol Vis Sci. 1979 December; 18(12):1278-80) and occurs in the human lens in the second decade of life. It is hereafter 16 referred to in this invention as "The red fluorophore of the human lens. It is a significant aspect of this invention.

In summary, this invention teaches a new physical parameter to the PBM effect. Whereas, the primary parametric values for the light source used in PBM have been wavelength and wave length regions, intensity and dose of the PBM light source; this invention adds another parameter—it suggests groups or emission bands of wavelengths which have designated amplitudes with emission maxima at designated wavelengths and having designated relative intensities.

Applicant has invented an ophthalmic lens that uses a synthetic version of the red fluorophore that occurs in the human lens in the seventh decade of life and which has an emission spectrum that, according to the invention, defines the action evolved by Nature to best affect PBM—that is, the optimum action spectrum.

It should be noted that medical scientists (N T Yu, Kuck J F and Askren C C, Invest. Ophthalmol Vis Sci 18(12): 1278-80, 1979) reported a red fluorophore that begins to form in the human lens abruptly in the seventh decade of life. Later, it was reported (M Bando, N T Yu and J F R Kuck, Invest Ophthalmol Vis Sci 25:581-585, 1984) that this red fluorophore could be replicated by reacting oxidized 3 hydroxykynurenine with the (alpha) form of the crystallins of the human eye while under exposure to ultraviolet light. The authors did not associate this red fluorescence with PBM. According to the present invention the incorporation of this red fluorophore in a filter to effect PBM.

The fluorescence spectrum of the resulting product of the reaction between the oxidized product 3 hydroxykynurenine and the (alpha) form of the crystallins of the human eye—while under exposure to ultraviolet light—is shown in FIG. 2; and because of the details of this spectrum (the wavelengths at which the emission peaks occur and the relative intensity of these peaks) and the fact that this product represents a naturally-occurring fluorescent molecule that has been evolved by Nature, Applicant proposes this red fluorophore to have an ideal fluorescent emission spectrum that is tuned to maximize the PBM effect for protecting and repairing the retina from the damage caused by its exposure to sunlight.

BRIEF DESCRIPTION OF THE DRAWINGS

For a detailed description of the preferred embodiment of the invention, reference will now be made to the accompanying drawings wherein.

DETAILED DESCRIPTION OF THE INVENTION

The present invention discloses the use of a synthetic form of the red fluorophore of the human lens as an ingredient for light filters, such as sunglass lenses, to affect photobiomodulation. This fluorescence occurs abruptly—according to the investigators who discovered it; and its emission spectrum, for an excitation wavelength of 647 nm, is reproduced in FIG. 2 (Yu, 1979) emission spectrum.

This red fluorophore is to be synthesized (as described by M bando, N T Yu and J F R Kuck, Invest Ophthalmol Vis Sci 25:581-585, 1984) by the reaction of 3 Hydroxykyurenine with a-crystallin—in aqueous media and under Ultraviolet and high energy visible light. The red fluorophore may also be formed by the reaction of 3 Hydroxykyurenine and its glucosides or any of the uv-absorbing chromophores of the human lens with a-crystallin or with compounds associated with a-crystallin over the age of 70. The red fluorophore may also be formed by the reaction of tryptophan with a crystallin under the action of UV and HEV light. The fluorescence spectrum of this red fluorophore is shown in FIG. 2 (curve 1).

Figure 1:
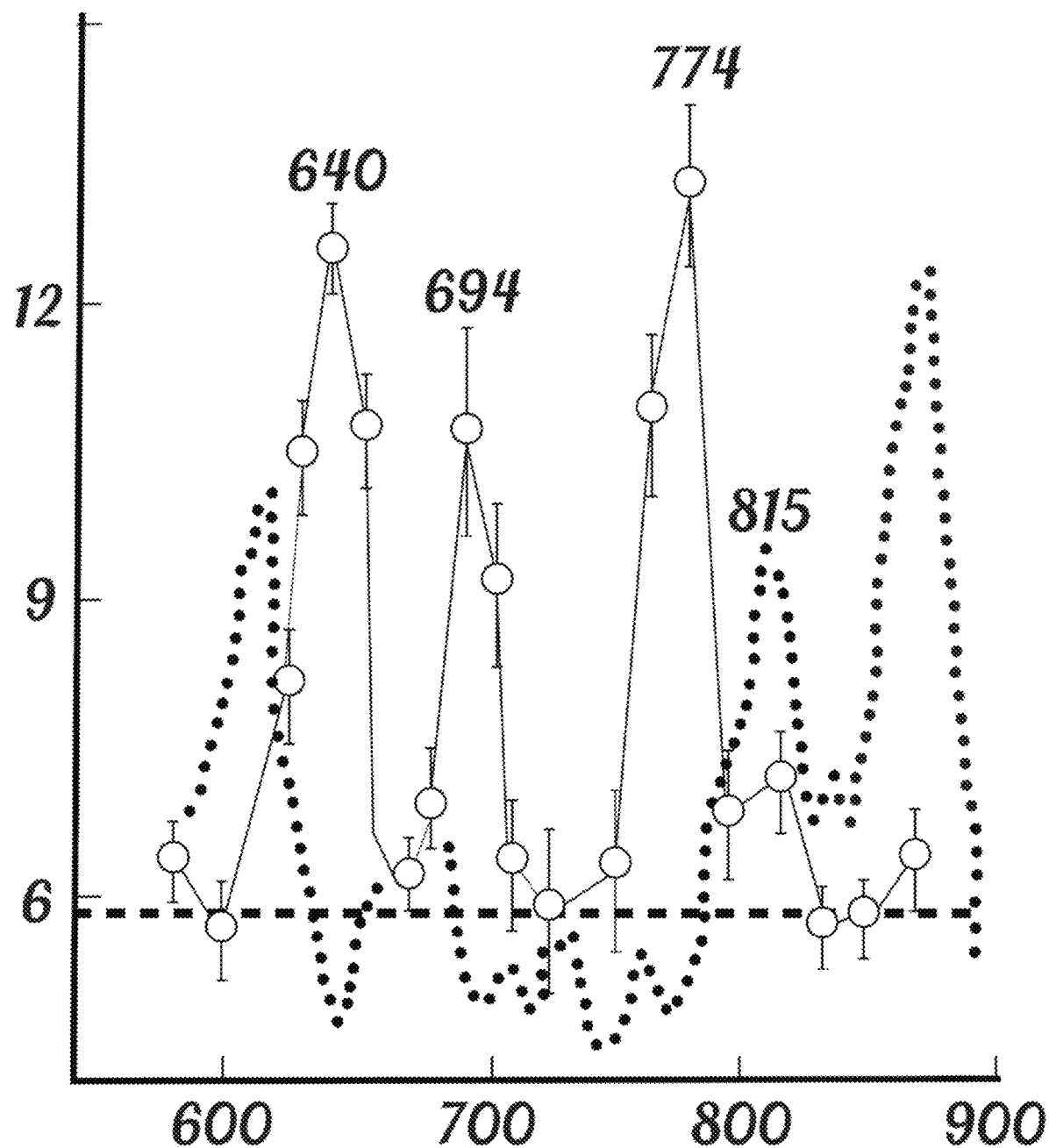
FIG. 1 is a diagram of an action spectra of cytochrome C.
Figure 2:
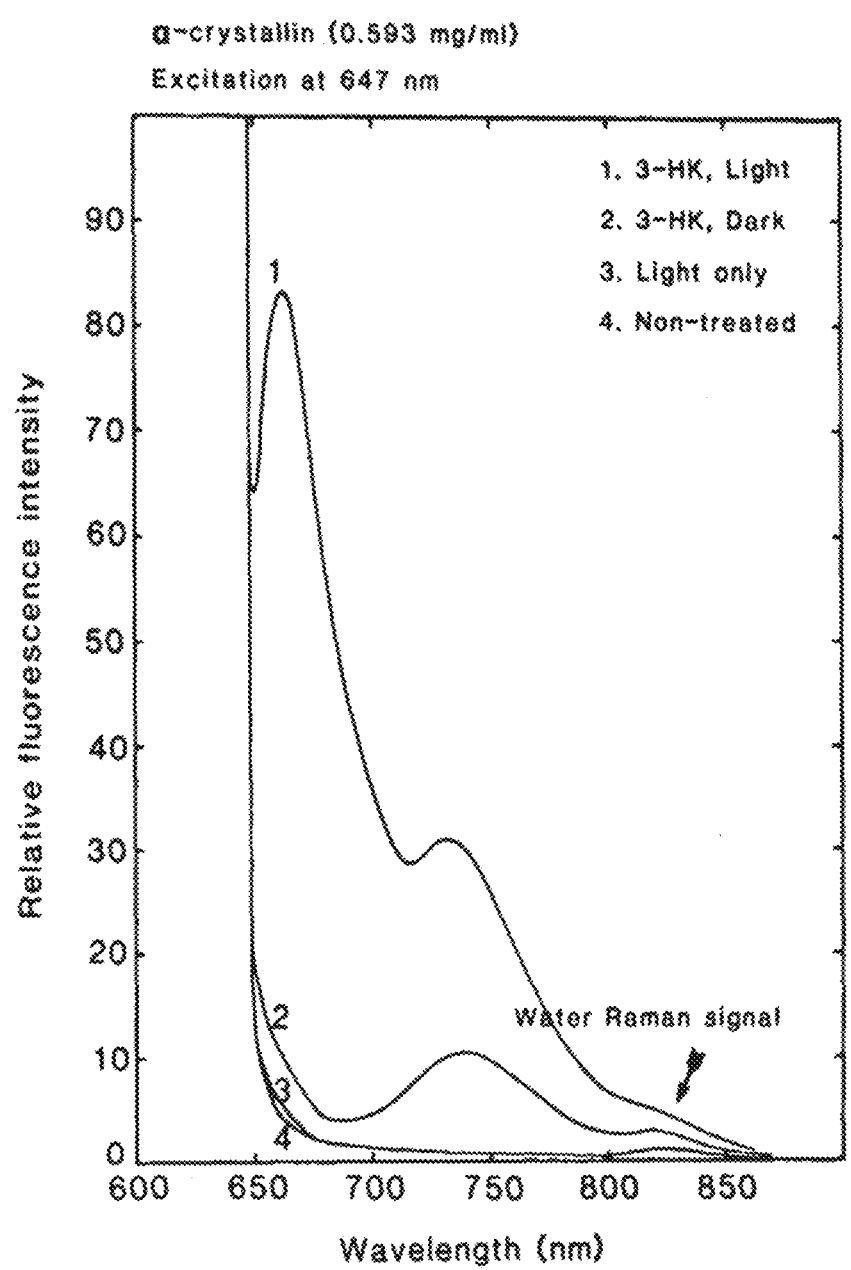
FIG. 2 is a diagram of the fluorescence spectrum of the red fluorophore of the human lens (Curve 1, 3-HK—light)

The following essential points about FIG. 2 and of this invention should be noted:

1) The fluorescence of the red fluorophore spans the wavelength range of about 600 nm to 900 nm—according to FIG. 2—the same wavelength range that is associated with PBM studies on humans exposed to red and near IR LED lights.
2) The fluorescence of FIG. 2 has a major peak at 670 nm and a secondary peak at around 730 nm-740 nm and a minor peak at around 825 nm.
'3) Applicant further claims in this invention that the red fluorophore of the ocular lens has evolved to provide wavelength-selective repair (photobiomodulation) to the retina.

According to the invention, there is claimed a relationship between the use of 670 nm light from LED light sources previously used by investigators (Joshua A. Chu-Tan, et al, International Journal of Photoenergy, Volume 2016, Article ID 2734139) to demonstrate the positive PBM health effects on the retina and the red fluorescence from the human lens that occurs naturally in the seventh decade of life and that also emits light with a maxima at 670 nm.

Furthermore, the invention underscores the fact that the fluorescence emission from the red fluorophore of the human lens is wavelength selective to optimize the repair of the retina for a sunlight environment. For example, the intensity of the emission of the red fluorophore of FIG. 2 at the wavelength of 670 nm is approximately 2.8 times the emission intensity at 735 nm and about 12 times the intensity at 825 nm.

The invention hereby discloses the use of a synthetic version of the red fluorophore of the human lens incorporated into an ophthalmic lens to convert sunlight into the fluorescence characterized by FIG. 2 of this application—thereby irradiating the retina with red and near IR light that has higher intensities at the correct wavelengths which are the hall marks of a reproducible PBM effect.

Description of a Preferred Embodiment

A synthetic form of the red fluorophore of the human lens is prepared according to the method of M Bando in M Bando, N T Yu and J F R Kuck, Invest Ophthalmol Vis Sci 25:581-585, 1984. As described in that reference, an aqueous suspension of the light-induced reaction product between oxidized 3 hydroxykynurenine and alpha-crystallin can be prepared.

Example 1

This is a theoretical example. An ophthalmic lens containing an aqueous suspension the red fluorophore can be prepared as follows: the aqueous suspension described above is combined with a waterborne primer resin such as one of the commercially-available formulations, like the Hauthaway HD6002 which is suitable for use as a primer coating for a polycarbonate ophthalmic lens.

Figure 3:
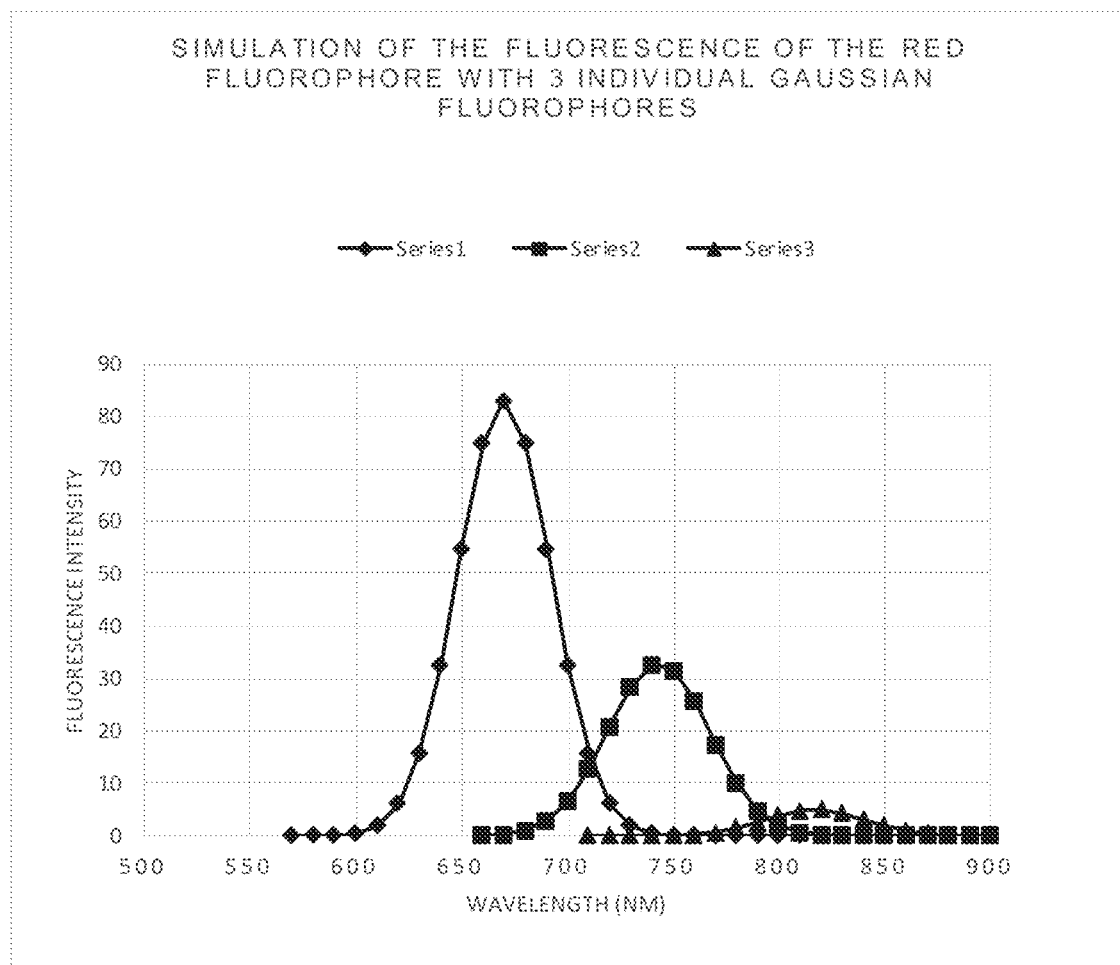
FIG. 3 is a simulation of the fluorescence of the red fluorophore of the human lens—using several individual gaussian bands to represent several arbitrary fluorescent molecules.

Upon evaporation of the solvents from the said primer resin, the resultant coating on the ophthalmic lens can absorb sunlight and cause a fluorescence like shown in FIG. 3.

While the invention described herein makes reference to a specific fluorescence emission spectrum that corresponds to a mature human lens, it is possible that the relative intensities of the emission spectra of the aged lenses changes slightly. For example, the relative peak emissions at 670 nm, 735 nm and at 825 nm may change slightly as well as the location of the peak emissions.

Description of an Alternative Preferred Embodiment

In an alternative preferred embodiment, the fluorescence emission spectrum of the red fluorophore of the human lens can be well-replicated by the superposition of the emission spectra of several fluorophores—for example quantum dots—whose respective peak emissions occur within a specific range of wavelengths and whose widths at half maximum also occur within a specific wavelength range.

A model for the emission spectrum of the red fluorophore of the reference, M bando, N T Yu and J F R Kuck, Invest Ophthalmol Vis Sci 25:581-585, 1984, and presented here for the first time, consists of 3 gaussian curves defined as $$I(\lambda) = A\exp(-((\lambda-\lambda_p)^2)/(2\sigma^2)) \qquad 1)$$

wherein $I(\lambda)$ is the emission as a function of the wavelength; exp is the exponential function; $\lambda$ is the variable wavelength in nanometers (nm); $\lambda_p$ is the wavelength where the individual gaussian curves are a maximum; and $\sigma$ is a parameter relating to the full width at half maximum as follows:

$$FWHM = 2.355\sigma. \qquad 2)$$

The equation 1) was entered into an Excel spreadsheet over the wavelength range from 570 nm to 900 nm for every 10 nm for 3 gaussian curves with the following parameters:

TABLE 1

| A Fluorescence Intensity (arbitrary units) | Ratio of Fluorescence Intensities at 670 nm to smaller bands | $\lambda_p$ | $\sigma$ | FWHM |
| --- | --- | --- | --- | --- |
| 83 | 83/83 = 1 | 670 nm | 22 nm | 51.8 nm |
| 33 | 83/33 = 2.5 | 743 nm | 24 nm | 56.5 nm |
| 4 | 83/5 = 16.6 | 817 nm | 24 nm | 56.5 nm |

Figure 4:
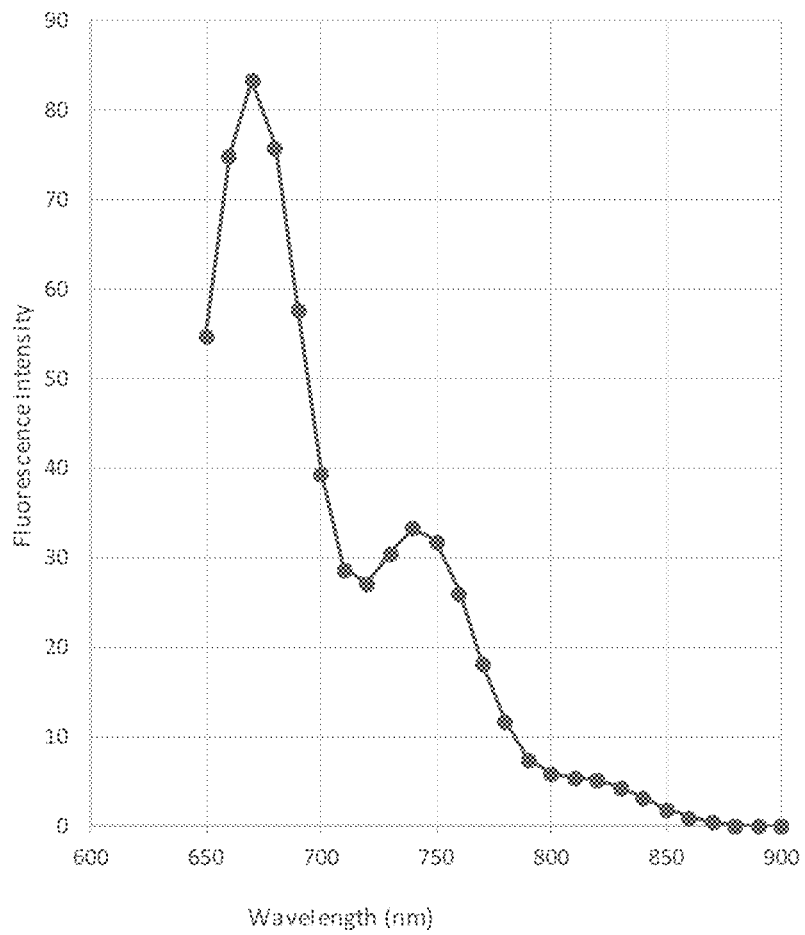
FIG. 4 is effective fluorescence derived from the superposition of the several gaussian bands representing the fluorescence of the several arbitrary fluorescent molecules.

The values above were used in equation 1 for each of the three gaussian curves that are shown in FIG. 3, and then were added together (superposed) as shown in FIG. 4 so as to provide a good fit with the experimental curve of FIG. 2—the emission spectrum of the red fluorophore of the human lens.

A good fit is considered here to be one with a statistical R square value of 0.8 or greater and can be improved by anyone skilled in the art.

Example 2, therefore, illustrates that 3 fluorescent dyes whose emission spectra correspond 16 to Series 1, 2, and 3 respectively can be selected with the parameters of Table 1 and with the proper concentrations to correspond to the ratios of column 2 so as to closely replicate the emission spectrum of the red fluorophore of the human lens.

The model for the red fluorophore actually assumes 3 distinct fluorophores with emission bands characterized by the data of Table 1. With an oligomeric system such as the chromophore of the human lens, a three-component fluorescence system is common. The choice of 3 distinct quantum dots as described below in Example 2, is consistent with this assumption.

Because the ocular lens pigment continues to change after the age of 70 and because its photochemical reaction with alpha-crystallin should be expected to continue, the parameters of Table 1 should be expected to change slightly with age and it is therefore within the context of this invention to claim small variances in the parameters—as shown in Table 2.

TABLE 2

| A Fluorescence Intensity (arbitrary units) | Ratio of Fluorescence Intensities at 670 nm to smaller bands | $\lambda_p$ | $\sigma$ | FWHM |
| --- | --- | --- | --- | --- |
| 83 | 83/83 = 1 | 670 nm +/−10 nm | 22 nm +/−2 nm | 51.8 nm +/−5 nm |
| 33 | 83/33 = 2.5 +/−.5 | 743 nm +/−10 nm | 24 nm +/−2 nm | 56.5 nm +/−5 nm |
| 4 | 83/5 = 16.6 +/−4 | 817 nm +/−10 nm | 24 nm +/−2 nm | 56.5 nm +/−5 nm |

Example 2

An optically clear dispersion (low light scatter) of quantum dots in an organic solvent was prepared in order to determine the concentrations of the individual quantum dots so as to result in a superposition of emission spectra that approximate the emission spectrum of the red fluorophore of the human lens. The procedure is as follows: In 2 ml of heptane, a mixture of 480 µg of CdTe/ZnS core/shell quantum dots 680 nm (Nano Optical Materials QD680-OS), 80 µg of CdSeTe/ZnS core/shell quantum dots 740 nm (Nano Optical Materials QD740-OS) and 32 µg of CdSeTe/ZnS core/shell quantum dots 820 nm (Nano optical Materials QD820-OS) were dispersed. These concentrations were used to prepare the optical coating of Example 3.

Example 3

A poly(methyl methacrylate) coating was prepared from the stock solutions as follows:

In 1 ml of dichloromethane 100 mg of poly(methyl methacrylate) (PMMA) (Aldrich, MW: 120,000) was dissolved at room temperature. To the obtained solution 720 µg of CdTe/ZnS core/shell quantum dots 680 nm (Nano Optical Materials QD680-OS), 120 µg of CdSeTe/ZnS core/shell quantum dots 740 nm (Nano Optical Materials QD740-OS) and 48 µg of CdSeTe/ZnS core/shell quantum dots 820 nm (Nano optical Materials QD820-OS) were added and stirred for 10 minutes at room temperature to form a homogenous solution. The quantum dot/PMMA mixture was applied to a glass surface with a pipette and air dried at room temperature to give a transparent film. Four consecutive layers were deposited on top of each other the same way. Finally, the quantum dot/PMMA coating was cured at 60 C for 30 minutes. The fluorescence of the obtained coating was recorded with a spectrofluorometer at excitation wavelengths of 450 nm and 647 nm respectively and displayed in FIG. 5 and FIG. 6 respectively.

Figure 5:
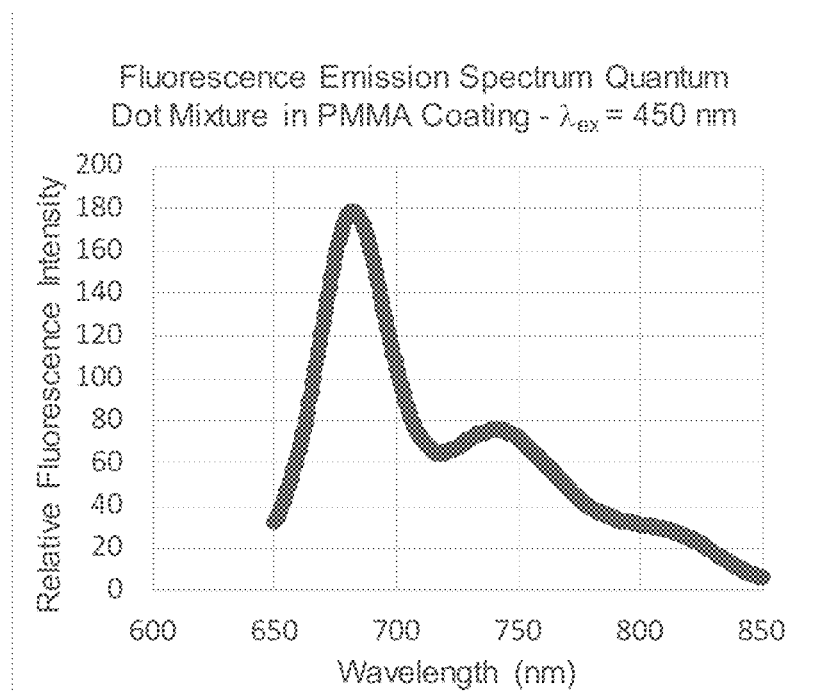
FIG. 5 is the fluorescence emission spectrum of a specific quantum dot mixture in a PMMA Coating with an excitation wavelength of 450 nm.
Figure 6:
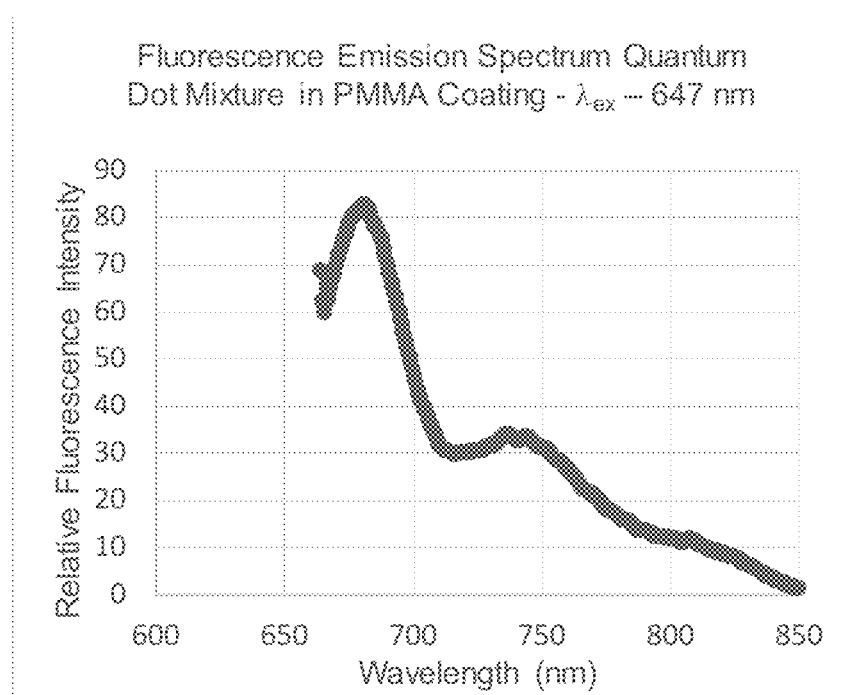
FIG. 6 is the fluorescence emission spectrum of a specific quantum dot mixture in a PMMA Coating with an excitation wavelength of 647 nm

FIGS. 5 and 6 fit the emission of the red fluorophore approximately and the goodness of fit between these spectra can be improved by further variation of the relative concentrations and then characterized by linear or non-linear regression techniques familiar to those skilled in the art with R square values of greater than or equal to 0.5.

The above description is illustrative of the preferred embodiment and many modifications may be made by those skilled in the art without departing from the invention whose scope is to be determined from the literal and equivalent scope of the claims below.

What is claimed is:

1. A photobiomodulation system to repair the retina of a human subject comprising one or more light sources wherein the emission spectrum of the light reaching the eye of the subject by the light source or sources is represented by peak emission wavelengths that are 670 nm+/−10 nm, 743 nm+/−10 nm, and 817 nm+/−10 nm; ratio of fluorescence intensities at 670 nm to the subsequently-smaller intensity bands are 2.5+/−0.5 and 16.6+/−4; and full widths at half-maximum are 51.8 nm+/−5 nm, 56.5 nm+/−5 nm and 56.5 nm+/−5 nm.

* * * * *